United States Patent [19]

Ho

[11] Patent Number: 4,529,724
[45] Date of Patent: Jul. 16, 1985

[54] 6H-INDOLO[2,1-C][1,4]BENZODIAZEPINES AND 12-OXO DERIVATIVES USEFUL AS ANTIHYPERTENSIVES

[75] Inventor: Chih Y. Ho, Lansdale, Pa.

[73] Assignee: McNeilab, Inc., Fort Washington, Pa.

[21] Appl. No.: 540,262

[22] Filed: Oct. 11, 1983

[51] Int. Cl.³ .................... A61K 31/55; C07D 487/04
[52] U.S. Cl. .............................. 514/215; 260/239.3 P; 260/245.7; 548/421; 548/492
[58] Field of Search ...................... 260/239.3 P, 245.7; 548/421; 424/274

[56] References Cited

PUBLICATIONS

Journal of Medicinal Chemistry, 1980, vol. 23, No. 4, pp. 462–465, W. B. Wright et al.
E. E. Garcia et al., Journal of Heterocyclic Chemistry, vol. 7, pp. 1161–1163, (1970).

Primary Examiner—Robert T. Bond
Attorney, Agent, or Firm—David J. Levy

[57] ABSTRACT

Compounds of the present invention are of the formula (I):

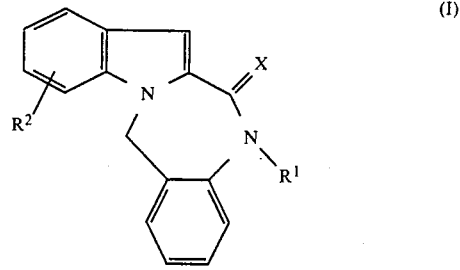

wherein X is oxygen or two hydrogens, $R^1$ is a variety of substituents or hydrogen and $R^2$ is hydrogen, alkoxy, alkyl, $CF_3$, halogen, $NO_2$, OH or dialkylamino. The compounds are useful as blood pressure lowering agents and may be used in the treatment of hypertension. Also, part of the invention are pharmaceutical compositions and uses and intermediates for compounds of formula (I).

10 Claims, No Drawings

6H-INDOLO[2,1-C][1,4]BENZODIAZEPINES AND 12-OXO DERIVATIVES USEFUL AS ANTIHYPERTENSIVES

Incidental to the study of acyl indoles, an indolo[2,1-c][1,4]benzodiazepine was prepared without mention of utility, see E. E. Garcia et. al. in the Journal of Heterocyclic Chemistry, Volume 7, pages 1161–1163 (1970).

SUMMARY OF THE INVENTION

Various indolo-benzodiazepines have been found to significantly lower blood pressure and are thus useful in the treatment of hypertension in animals such as humans. The compounds of the invention are of the following formula (I):

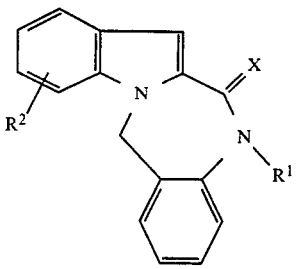

wherein X represents an oxo functionality or two hydrogen atoms, $R^1$ represents hydrogen or alkyl optionally with various substituents and $R^2$ is hydrogen or an alkoxy group. Also, part of the present invention are pharmaceutical compositions containing such compounds and methods for the treatment of hypertension with the pharmaceutical compositions and intermediates.

DETAILED DESCRIPTION OF THE INVENTION

The compounds of the invention are of the following formula (I):

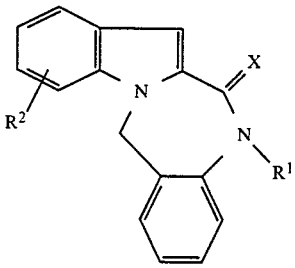

wherein

X is an oxygen atom or two hydrogen atoms;

$R^1$ is hydrogen, alkyl, alkyl substituted by a cyano, amino, alkylamino, dialkylamino or oxirane group, an alpha-(N-[2-(3,4-dimethoxyphenyl)ethyl]aminomethyl)-beta-ethanol group or a 3-(2-methylpropoxy)-2-(1-pyrrolidinyl)propyl group; and $R^2$ is hydrogen, alkoxy, alkyl, trifluoromethyl, halo, nitro, hydroxy or dialkylamino, and the pharmaceutically-acceptable acid-addition salts thereof.

In more detail, $R^1$ may be hydrogen; alkyl of about 1 to 12 carbons, such as methyl, ethyl, n-propyl, iso-propyl, n-butyl, sec-butyl, iso-butyl, t-butyl, pentyl or hexyl; alkyl of about 1 to 6 carbons substituted by a cyano, amino, alkylamino of about 1 to 5 carbons, dialkylamino of about 2 to 10 carbons or an oxirane (epoxide) group; an alpha-(N-[2-(3,4-dimethoxyphenyl)ethyl]aminomethyl)-beta-ethanol group; or a 3-(2-methylpropoxy)-2-(1-pyrrolidinyl)propyl group.

$R^2$, in particular, is hydrogen; alkoxy of about 1 to 6 carbons such as methoxy, ethoxy or iso-propoxy; alkyl of about 1 to 6 carbons such as methyl, ethyl or tert-butyl; trifluoromethyl; halo such as fluoro, chloro, bromo or iodo; nitro; hydroxy; or dialkylamino of about 2 to 10 carbons such as dimethylamino and N-ethyl-N-methylamino.

The salts of benzodiazepines of formula (I), particularly when X is two hydrogens and/or there is an amine function in $R^1$ or $R^2$, are those formed with physiologically acceptable acids such as hydrochloric, hydrobromic, hydroiodic, perchloric, sulfuric, nitric, phosphoric, acetic, propionic, glycolic, lactic, pyruvic, malonic, succinic, maleic, fumaric, malic, tartaric, citric, benzoic, cinnamic, mandelic, methanesulfonic, ethanesulfonic, hydroxyethanesulfonic, benzenesulfonic, p-toluenesulfonic, cyclohexanesulfamic, salicylic, p-aminosalicylic, 2-phenoxybenzoic, 2-acetoxybenzoic or a salt made with saccharin. It is understood that compounds of formula (I) may exist in various isomeric forms, e.g., optical isomers formed in view of the different possible configurations of asymmetrical alkyl groups for $R^1$ such as 3-methyl-n-pentyl. The present invention includes all such individual isomers and racemates. In addition, compounds of Formula (I) may exist in hydrated and solvated forms and the invention includes all such forms.

Representative compounds of the present invention are the following: 6H-indolo[2,1-c][1,4]benzodiazepin-12(11H)-one; 11-methyl-6H-indolo[2,1-c][1,4]benzodiazepin-12(11H)-one; 11,12-dihydro-6H-indolo[2,1-c][1,4]benzo diazepine; 11,12-dihydro-11-oxiranylmethyl-6H-indolo[2,1-c][1,4]benzodiazepine; alpha-(N-[2-(3,4-dimethoxyphenyl)ethyl]aminomethyl)-11,12-dihydro-6H-indolo[2,1-c][1,4]benzodiazepine-11-ethanol; 11,12-dihydro-11-[3-(2-methylpropoxy)-2-(1-pyrrolidinyl)propyl]-6H-indolo[2,1-c][1,4]benzodiazepine; 11,12-dihydro-11-dimethylaminopropyl-6H-indolo[2,1-c]-[1,4]benzodiazepine; 11-cyanomethyl-6H-indolo[2,1-c][1,4]benzodiazepine-12(11H)one; N,N-dimethyl-6H-indolo[2,1-c][1,4]benzodiazepin-12(11H)-one-11-propanamine; 3-methoxy-6H-indolo[2,1-c][1,4]benzodiazepin-12(11H)-one; 3-methoxy-N,N-dimethyl-6H-indolo[2,1-c][1,4]-benzodiazepin-12(11H)-one-11-propanamine; 11-hexyl-6H-indolo[2,1-c][1,4]benzodiazepin-12(11H)-one; and 11-hexyl-11,12-dihydro-6H-indolo[2,1-c][1,4]-benzodiazepine.

The compounds of formula (I) may be prepared by reacting an appropriately-substituted alkyl 2-indolecarboxylate of the formula (II) with 2-nitrobenzyl chloride to yield the ester (III) wherein Y is $NO_2$ which is then reduced to the corresponding amine of formula (III) where Y is $NH_2$ and cyclized to the compound of formula (I) wherein X is oxygen and $R^1$ is hydrogen according to the following reaction scheme:

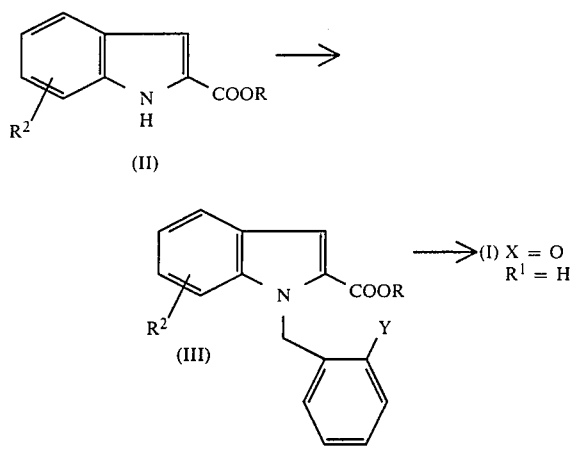

wherein R is alkyl of about 1 to 6 carbons, preferably about 1 to 3 carbons. Compounds of the formula (II) wherein $R^2$ is hydrogen, alkoxy, trifluoromethyl, halo, or dialkylamino may be prepared by the method of W. E. Noland in Organic Synthesis, Vol. 43, p. 40–45 (1963) using the appropriately substituted o-nitrotoluene as starting material. If $R^2$ is hydroxy, the methoxy indole may be prepared and deprotected with HBr or $BBr_3$ as known in the art. In addition, formula (II) compounds are known in the art and available commercially, see N. Bauman et al. in Biochemical Pharmacology, Vol. 18, pages 1241–1243 (1969) for $R^2$ as alkoxy, nitro, hydroxy, or halo; J. Bornstein et. al. in the Journal of the American Chemical Society, Vol. 79, pages 1745–1748 (1957) for $R^2$ as trifluoromethyl; F. L. Allen et. al. in Journal of the Chemical Society, pages 1283–1286 (1955) for $R^2$ as fluoro; U.S. Pat. Nos. 3,332,846, 4,053,624, 4,137,313, and 4,350,633; German OLS No. 1,948,507; and U.K. Patent Application No. 2,098,205 A published Nov. 17, 1982. Compounds of the formula (II) wherein R is alkyl may be prepared from the corresponding acids, i.e., R=H, by esterification with an alcohol and a catalytic amount of acid as known in the art. The $R^2$ substituent may be at the 4-, 5-, 6- or 7-position of the indole ring system.

In more detail, the reaction between the indole of formula (II) and 2-nitrobenzyl chloride may be conducted by first reacting the indole with a strong base such as sodium hydride at about −78° to 60° C. in a dry solvent, e.g. DMF. The thus-produced anion of the indole is reacted with 2-nitrobenzyl chloride at an initial temperature of about −78° to 25° C. and allowing the reaction to warm to room temperature. The ester (III) where Y is $NO_2$ is then converted to the amine of the formula (III) where Y is $NH_2$ by reduction, e.g., by catalytic reduction with $H_2$ in a solvent such as methanol using a noble metal such as palladium or Raney nickel catalyst. The amino ester (III) where Y is $NH_2$ is then converted to the lactam of formula (I) wherein X is oxygen and $R^1$ is hydrogen by heating at about 100° to 200° C. with an amide-forming catalyst such as 2-hydroxypyridine. For compounds of formula (I) wherein X is two hydrogen atoms, the corresponding X=O compound may be reduced with a hydride reducing agent such as $BH_3$ or lithium aluminum hydride at a temperature of about 25° to 100° C. For $R^1$ moieties other than hydrogen, a compound of formula (I) wherein X is oxygen or two hydrogens, i.e., before or after reduction, may be reacted to form the N-anion and then reacted with a compound of the formula $R^1$—LG wherein LG is a tosylate, mesylate or a halogen and the halogen is particularly iodine, bromine, or chlorine. The anion may be formed with a strong base such as a metal hydride, e.g., sodium hydride or a Grignard may be formed, e.g., with a reagent such as ethyl magnesium bromide, at about 0° to 180° C., e.g., at room temperature. The reaction with the $R^1$—LG compound may take place at 0° to 180° C.

The compounds of the invention have been found to be useful in the treatment of hypertension as shown by the Rodent Antihypertensive Model. This test evaluates compounds for effects on arterial pressure and heart rate. In this test, the arterial pressure of adult spontaneously hypertensive rats (SHR) (Charles River) is monitored directly via an aortic cannula. The SHR rats are anesthetized with an inhalation anesthetic (methoxyflurane). The left carotid artery is isolated and cannulated. The tip of the cannula is advanced to the aorta and the cannula is exteriorized behind the neck at the level of the scapula. Animals are placed in individual cages and allowed to recover from the anesthetic and are kept unrestrained. The arterial cannula is connected to the pressure transducer which is attached to the recorder. Heart rate is determined from the arterial pressure recording. The test compounds are administered either orally by gavage or by intraperitoneal injection. The arterial pressure and heart rate are monitored for a minimum of 24 hours. A test compound is considered to be active as an antihypertensive agent if the mean arterial pressure (MAP) indicates a fall of >15 mm of Hg. Each animal serves as its own control.

Test results for compounds of the invention or an acid-addition salt thereof are shown in the following Table 1:

TABLE 1

| | Maximum change in Blood Pressure (in mm of Hg) | |
|---|---|---|
| Invention compound of | p.o. (100 mg/kg) | i.p. (30 mg/kg) |
| Example 1 | variable or none | −42 |
| Example 2 | −26 | −34 |
| Example 3 | −15 | −65 |
| Example 4 | −27 | −22 |
| Example 5 | −18 | −33 |
| Example 6 | −33 | −74 |
| Example 7 | −31 | −73 |
| Example 9 | −32 | −60 |
| Example 11 | −13 | −46 |
| Example 12 | −18 | −25 |
| Example 13 | −25 | −40 |

Also part of the present invention are pharmaceutical compositions and methods for the treatment of hypertension using such compositions. To prepare the pharmaceutical compositions of this invention, one or more compounds or salt thereof of the invention as the active ingredient, is intimately admixed with a pharmaceutical carrier according to conventional pharmaceutical compounding techniques, which carrier may take a wide variety of forms depending on the form of preparation desired for administration, e.g., oral, topical or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, from about 10 to about 500 mg of the active ingredient, and, preferably, from about 25 to about 100 mg.

For the treatment of hypertension in a mammal, particularly a human, one or more compounds of the invention or acid-addition salts thereof, may be administered in an amount of about 10 to 100 mg per kg of body weight per day orally, preferably about 25 to 75 mg/kg or parenterally, e.g. i.p., intravenously, intramuscularly or rectally, in an amount of about 0.5 to 10 mg/kg per day, preferably about 2 to 5 mg/kg. The daily dosage may be divided into 2-4 equal individual doses.

Also, part of the present invention are the intermediates of the formula (III) wherein Y is $NO_2$ or $NH_2$.

In the following examples and throughout the specification, the following abbreviations may be used: mg (milligrams); g (grams); kg (kilograms); ml (milliliters); mmole (millimoles); M (molar); N (normal); psi (pounds per square inch); mp (melting point); bp (boiling point); meq (milliequivalents); E (trans); Z (cis); $Et_2O$ (diethyl ether); EtOAc (ethyl acetate); MeOH (methanol); EtOH (ethanol); i-PrOH (iso-propanol); LAH (lithium aluminum hydride); THF (tetrahydrofuran); DMF (dimethylforamide); p.o. (per os, orally); i.p. (intraperitoneal); and C,H,N,O, etc. (the chemical symbols for the elements). Unless otherwise indicated, all temperatures are reported in °C. (degrees centigrade).

EXAMPLE 1

6H-Indolo[2,1-c][1,4]benzodiazepin-12(11H)-one

Formula (I): X=O; $R^1$=H; $R^2$=H

A mixture of 5.69 g (0.237 mole) of sodium hydride and 200 ml of dry DMF was stirred under an atmosphere of $N_2$ and cooled with an ice-water bath. A solution of 42.7 g (0.226 mole) of ethyl 2-indolecarboxylate in 150 ml of dry DMF was added with stirring over a period of 1.5 hours and stirring was continued overnight at room temperature. The resulting solution was cooled to −65° C. with a dry ice-acetone bath and a solution of 50 g (0.29 mole) of 2-nitrobenzyl chloride in 60 ml of dry DMF was added. The reaction mixture was allowed to stir at room temperature overnight and then poured into a mixture of ice and water. A yellow solid was obtained by filtration and recrystallized from ethanol.

The above obtained yellow solid and 2 g of 10% Pd/C in 450 ml of MeOH was hydrogenated under 50 psi hydrogen pressure at room temperature until the uptake of hydrogen ceased. The catalyst was removed by filtration and the filtrate was evaporated in vacuo to yield a brown solid which was combined with 300 ml of xylene and 7 g of 2-hydroxypyridine and heated at reflux with a Dean-Stark trap for 48 hours. The title compound was obtained by filtration and recrystallized from i-PrOH/DMF to yield a white solid, mp 270°-272° C.

Elemental Analysis: Calculated for $C_{16}H_{12}N_2O$: C, 77.40; H, 4.87; N, 11.28. Found: C, 77.50; H, 5.04; N, 11.66.

EXAMPLE 2

11-Methyl-6H-indolo[2,1-c][1,4]benzodiazepin-12(11H)-one

Formula (I): X=O; $R^1$=$CH_3$; $R^2$=H

In a dry three-necked flask under nitrogen was placed 1.44 g (0.03 mole) of 50% oily NaH. The hydride was washed twice with hexane and 70 ml of dry DMF was added. A solution of 6.2 g (0.025 mole) of 6H-indolo[2,1c][1,4]benzodiazepin-12(11H)-one, the product of Example 1, in 70 ml of DMF was added dropwise and stirring continued for 4 hours at room temperature. Excess methyl iodide (3 ml) was added, the mixture stirred overnight and then poured into ice-water. An off-white solid (7.46 g) was obtained by filtration and recrystallized from EtOAc-EtOH-DMF and then from EtOAc to give the title compound, a white solid, mp 188.5°-190° C.

Elemental Analysis: Calculated for $C_{17}H_{14}N_2O$: C, 77.84; H, 5.38; N, 10.68. Found: C, 77.78; H, 5.43; N, 10.66.

EXAMPLE 3

11,12-Dihydro-6H-indolo[2,1-c][1,4]benzodiazepine

Formula (I): X=H,H; $R^1$=H; $R^2$=H

A mixture of 7.1 g (0.0286 mole) of 6H-indolo[2,1-c][1,4]benzodiazepin-12(11H)-one, the product of Example 1, 2.17 g (0.057 mole) of LAH and 100 ml of THF was refluxed for 5 hours under a nitrogen atmosphere. The reaction mixture was cooled to room temperature followed by the addition of 2.1 ml of water, 2.1 ml of 15% NaOH solution and 6.3 ml of water. The white solid obtained after 0.5 hour was filtered to give a light yellow filtrate which was concentrated in vacuo to give 6.54 g of off-white solid. Recrystallization from i-PrOH/EtOAc gave the title compound as a white solid, mp 176°-177° C.

Elemental Analysis: Calculated for $C_{16}H_{14}N_2$: C, 82.02; H, 6.02; N, 11.96. Found: C, 81.97; H, 6.07; N, 11.93.

EXAMPLE 4

11,12-Dihydro-11-oxiranylmethyl-6H-indolo[2,1-c][1,4]benzodiazepine

Formula (I): X=H,H; $R^1$=$CH_2CH(O)CH_2$

A mixture of 20.00 g (0.085 moles) of 11,12-dihydro-6H-indolo[2,1-c][1,4]benzodiazepine, the product of Example 3, and 200 ml of THF was treated dropwise with 40 ml (0.120 mole) of 3M $CH_3CH_2MgBr$ in $Et_2O$ under an atmosphere of nitrogen. Evolution of ethane was observed. With continued stirring at room temperature, 10 ml (0.130 moles) of epichlorohydrin were added dropwise over a period of 10 minutes. After stirring for about 30 minutes the reaction mixture was poured into 225 ml of saturated aqueous NaCl. The organic phase separated and the aqueous phase was extracted with two 75 ml portions of $Et_2O$. The organic phases were combined, washed with saturated NaCl and dried over anhydrous $K_2CO_3$. Removal of solvent in vacuo yielded 27 g of an oil which was dissolved in 100 ml of dry THF and added dropwise to a suspension of 6.15 g (0.128 moles) of 50% NaH/mineral oil in 100 ml of THF under a nitrogen atmosphere. The reaction was stirred overnight and 2.0 g of additional NaH oil suspension were added. After about 1 hour, the mixture was filtered through diatomaceous earth to remove NaCl and NaH. The filtrate was concentrated in vacuo to yield 25.4 g of red brown oil which slowly solidified. The solid was broken up and washed with a small amount of MeOH to obtain 22.15 g of an off white powder which was recrystallized from EtOH/chloroform to give 18.6 g of yellow crystals. The crystals were washed with hexane and recrystallized from EtOAc twice to obtain the title compound as a white solid, mp 104°–107° C.

Elemental Analysis: Calculated for $C_{19}H_{18}N_2O$: C, 78.60; H, 6.25; N, 9.65. Found: C, 78.50; H, 6.26; N, 9.62.

EXAMPLE 5 alpha-(N-[2-(3,4-Dimethoxyphenyl)ethyl]aminomethyl)-11,12-dihydro-6H-indolo[2,1-c][1,4]benzodiazepine-11-ethanol (E)-2-butenedioate (2:1)

Formula (I): X=H,H; $R^1$=CH$_2$CHOHCH$_2$NH(CH$_2$)$_2$-3,4-(CH$_3$O)$_2$C$_6$H$_3$; $R^2$=H A mixture of 5.00 g (0.017 moles) 11,12-dihydro-1-oxiranylmethyl-6H-indolo[2,1-c][1,4]benzodiazepine, the product of Example 4, and 3.44 g (0.019 moles) of homoveratryl amine in 50 ml of solfolane was heated to 110° C. under a nitrogen atmosphere in an oil bath. Heating was continued overnight and on the second day the temperature was raised to 125° C. After 8 hours at 125° C. the reaction mixture was cooled to room temperature and the yellow reaction mixture poured into 250 ml of a 1:1 mixture of EtOAc and Et$_2$O. The mixture was washed with three 50 ml portions of distilled water and two 50 ml portions of saturated aqueous NaCl. The organic solution was dried over anhydrous K$_2$CO$_3$ and the solvent was removed in vacuo to give 24.91 g of pale yellow oil. The oil was dissolved in 70 ml of EtOAc, treated with 1.97 g (0.017 moles) of fumaric acid and heated to reflux. After cooling and standing overnight, 4.51 g of pale orange crystals were collected by filtration. Four recrystallizations from DMF/i-PrOH, yielded 3.47 g of pale yellow crystals, mp 204°–6° C.

Elemental Analysis: Calculated for $C_{31}H_{35}N_3O_5$: C, 70.30; H, 6.66; N, 8.06. Found: C, 70.01; H, 6.59; N, 8.06.

EXAMPLE 6

11,12-Dihydro-11-[3-(2-methylpropoxy)-2-(1-pyrrolidinyl)propyl]-6H-indolo[2,1-c][1,4]benzodiazepine 2-naphthalenesulfonate Formula (I): X=H,H; $R^1$=CH$_2$CH(1-pyrrolidinyl)CH$_2$OCH$_2$CH(CH$_3$)$_2$; $R^2$=H Sodium hydride (2.06 g of a 50% oil suspension) was washed with cyclohexane and 60 ml of toluene added to the washed hydride. The suspension was heated under gentle reflux and a mixture of 9.1 g of 11,12-dihydro-6H-indolo[2,1-c][1,4]benzodiazepine, prepared as in Example 3, and 9.5 g of N-(2-chloro-3-iso-butoxy)-propylpyrrolidine in 100 ml of toluene was added. The reaction mixture was heated at reflux for 3 hours and then quenched with water. The organic layer was separated and dried over anhydrous MgSO$_4$ and the solvent removed in vacuo to give a crude free base. The free base was treated with one equivalent of 2-naphthalenesulfonic acid in acetone to give an off-white solid. The acid addition salt was recrystallized from EtOH to yield the title compound as a colorless solid, mp 156°–157.5° C.

Elemental Analysis: Calculated for $C_{37}H_{43}N_3O_4S$: C, 71.01; H, 6.95; N, 6.71; S, 5.12. Found: C, 70.67; H, 6.92; N, 6.68; S, 5.22.

EXAMPLE 7

11,12-Dihydro-11-Dimethylaminopropyl-6H-indolo[2,1-c][1,4]-benzodiazepine (E)-2-butenedioate (1:1)

Formula (I): X=H,H, $R^1$=(CH$_2$)$_3$N(CH$_3$)$_2$, $R^2$=H

Into a three necked flask equipped with an addition funnel and a magnetic stirrer and under a nitrogen atmosphere was placed 0.68 g of NaH and 20 ml of dry DMF. The flask was cooled in an ice-water bath and then a solution of 4.4 g of 11,12-dihydro-6H-indolo[2,1-c][1,4]benzodiazepine, the product of Example 3, in 20 ml of dry DMF was added dropwise over a period of 30 minutes. The resulting solution was stirred without cooling for 4 hours and then 3.4 g of N,N-dimethyl-3-chloropropanamine in 20 ml of DMF added. The resulting reaction solution was stirred at 45° C. for three days and then was poured into an ice-water mixture. The aqueous solution was extracted with EtOAc three times. The organic layers were combined and then was washed with saturated aqueous NaCl solution. Removal of solvent gave the crude product as an oil. The crude product was dissolved in MeOH and one equivalent of fumaric acid was added to give the fumarate salt. The salt was recrystallized from MeOH to yield a colorless solid, mp 171°–180° C.

Elemental Analysis: Calculated for $C_{21}H_{25}N_3 \cdot C_4H_4O_4$: C, 68.95; H, 6.71; N, 9.65. Found: C, 68.89; H, 6.72; N, 9.64.

EXAMPLE 8

11-(Cyanomethyl)-6H-indolo[2,1-c][1,4]benzodiazepin-12(11H)-one

Formula (I): X=O, $R^1$=CH$_2$CN, $R^2$=H

Into a dry flask equipped with an addition funnel and a magnetic stirrer and under a N$_2$ atmosphere was placed 1.2 g of NaH and 80 ml of dry DMF. The mixture was stirred for 12 hours at 25° C. After the addition of a solution of 11.2 g of 6H-indolo[2,1-c][1,4]benzodiazepin-12(11H)-one, the product of Example 1, in 140 ml of dry DMF, the reaction mixture was cooled to 0° C. and 7.2 ml of chloroacetonitrile was added. The mixture was stirred at 25° C. for an additional four hours and then was poured into ice-water. A light yellow brown solid was obtained by filtration. The solid was recrystallized from CH$_3$CN/DMF, to yield pure title compound, mp 243.5°–245° C.

Elemental Analysis: Calculated for $C_{18}H_{13}N_3O$: C, 75.25; H, 4.56; N, 14.62. Found: C, 75.01; H, 4.66; N, 14.84.

EXAMPLE 9

N,N-Dimethyl-6H-indolo[2,1-c][1,4]benzodiazepin12(11H)-one-11-propanamine oxalate Formula (I): X=O, $R^1$=CH$_2$CH$_2$CH$_2$N(CH$_3$)$_2$; $R^2$=H Into a dry flask equipped with an addition funnel and a magnetic stirrer under N$_2$ atmosphere, was introduced 1.02 g of NaH and 80 ml of DMF. The mixture was stirred while a solution of 8.4 g of 6H-indolo[2,1- c][1,4]benzodiazepine-12(11H)-one, the product of Example 1, in 80 ml of DMF were added. Stirring was continued for 12 hours and followed by the addition of 10 g of N,N-dimethyl-3-chloropropanamine. The resulting reaction mixture was stirred 12 hours and then was poured into an ice-water mixture. The aqueous solution was extracted with EtOAc three times. The organic layers were combined and washed with NaCl solution and dried over anhydrous $Na_2SO_4$. Removal of the solvent in vacuo gave a yellow oil. The oil was dissolved in EtOH and treated with one equivalent of oxalic acid to yield a white solid. The solid was recrystallized from MeOH to afford coloress crystalline oxalate salt, mp 188°–190° C. (dec).

Elemental Analysis: Calculated for $C_{21}H_{23}N_3O \cdot C_2H_2O_4$: C, 65.24; H, 5.95; N, 9.92. Found: C, 65.04; H, 6.02; N, 9.78.

EXAMPLE 10

3-Methoxy-6H-indolo[2,1-c][1,4]benzodiazepin-12(11H)-one

Formula (I): X=O, $R^1$=H, $R^2$=3-$OCH_3$

Into a three necked flask under an $N_2$ atmosphere was added 13.3 g of NaH (washed with hexane) and 280 ml of dry DMF. The mixture was cooled to 7° C. and then 65.9 g of ethyl 5-methoxy-indole-2-carboxylate in 350 ml of DMF was added at such a rate that the temperature was kept below 10° C. The reaction flask was then cooled with an ice-MeOH bath and a solution of 51.6 g of 2-nitrobenzyl chloride in 85 ml of DMF was added. The temperature was kept below −5° C. for 30 minutes and then raised to 25° C. for 12 hours. The reaction mixture was poured into 600 ml of ice-water. The nitrobenzyl indole was collected and recrystallized once from EtOH to yield a solid, mp 125° C. A Parr shaker bottle was charged with 17.7 g of the nitrobenzyl indole, 250 ml of EtOH and 2 g of Raney Nickel which had been prewashed three times with EtOH, and 60 psi hydrogen pressure. The Parr bottle was heated with a lamp to about 60° C. and shaken until hydrogen absorption ceased. The catalyst was removed by filtration and the solvent was evaporated on a rotary evaporator. The residual product was treated with 2 g of 2-hydroxypyridine and heated to reflux overnight in xylene. The xylene solution was cooled to 25° C. and the solid title product was obtained by filtration. The pure product was obtained by recrystallization from in DMF, mp 273°–274° C.

Elemental Analysis: Calculated for $C_{17}H_{14}N_2O_2$: C, 73.37; H, 5.07; N, 10.07. Found: C, 73.23; H, 5.13; N, 10.06.

EXAMPLE 11

3-Methoxy-N,N-dimethyl-6H-indolo[2,1-c][1,4]benzodiazepin-12(11H)-one-11-propanamine E-(2)-butenedioate (1:1)

Formula (I): X=O, $R^1$=$(CH_2)_3N(CH_3)_2$, $R^2$=3-$OCH_3$

Into a dry three necked flask equipped with an addition funnel and magnetic stirrer under an $N_2$ atmosphere was placed 0.56 g of NaH and 25 ml of dry DMF. The flask was cooled in an ice-water bath and then 5.28 g of 3-methoxy-6H-indolo[2,1-c][1,4]benzodiazepin-12(11H)-one, the product of Example 10, and 25 ml of DMF were added. After stirring for 4 hours at 25° C., 4.5 g of N,N-dimethyl-3-chloropropanamine were added and the reaction mixture was stirred at 25° C. overnight. The reaction mixture was poured into an ice-water mixture and the aqueous solution was extracted with $CH_2Cl_2$ three times. The organic layers were combined and washed with water, saturated NaCl, and then dried over anhydrous $K_2CO_3$. Removal of the solvent gave a crude product which was dissolved in MeOH and treated with one equivalent of fumaric acid to give an off-white solid, which was recrystallized from MeOH to yield a colorless crystalline solid, mp 215°–217° C.

Elemental Analysis: Calculated for $C_{22}H_{25}N_3O_2 \cdot C_4H_4O_4$: C, 65.12; H, 6.10; N, 8.76. Found: C, 64.91; H, 6.24; N, 8.84.

EXAMPLE 12

11-Hexyl-6H-indolo[2,1c][1,4]benzodiazepin-12(11H)-one

Formula (I): X=O,$R^1$=$(CH_2)_5CH_3$,$R^2$=H

Into a flask under a nitrogen atmosphere was placed 1.44 g of NaH and 80 ml of DMF. To the mixture was added 12.4 g of 6H-indolo[2,1-c][1,4]benzodiazepin-12(11H)-one, the product of Example 1. The resulting reaction mixture was stirred 2.5 hours at 25° C. and then 11 ml of 1-bromohexane was added. After stirring overnight, the reaction was poured into an ice-water mixture and an off-white solid was obtained by filtration. The title compound was obtained by recrystallization from MeOH, mp 115°–117° C.

Elemental Analysis: Calculated for $C_{22}H_{24}N_2O$: C, 79.48; H, 7.28; N, 8.42. Found: C, 79.42; H, 7.32; N, 8.39.

EXAMPLE 13

11-Hexyl-11,12-dihydro-6H-indolo[2,1-c][1,4]benzodiazepine

Formula (I): X=H,H, $R^1$=$(CH_2)_5CH_3$, $R^2$=H

To a mixture of 8 g of 11-hexyl-6H-indolo[2,1-c][1,4]benzodiazepin-12(11H)-one, the product of Example 12, 1.5 g of lithium aluminum hydride and 100 ml of THF were added and the mixture was heated to reflux for 4 hours. The reaction mixture was cooled to 0° C. and then 1.5 ml of water, 1.5 ml of 15% NaOH solution and 4.5 ml of water were sequentially added. The resultant white solid was filtered off and the solvent was stripped off to give the titled compound. Recrystallization from i-PrOH gave a colorless solid, mp 45° C.

Elemental Analysis: Calculated for $C_{22}H_{26}N_2$: C, 82.97; H; 8.23; N, 8.80. Found: C, 83.00; H, 8.24; N, 8.72.

What is claimed is:

1. An indolo[2,1-c][1,4]benzodiazepine of the following formula (I):

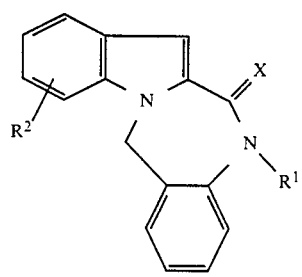

wherein
X is an oxygen atom or two hydrogen atoms;

$R^1$ is hydrogen, alkyl of 1 to 12 carbons, alkyl of 1 to 6 carbons substituted by a cyano, amino, alkylamino of 1 to 5 carbons, dialkylamino of 2 to 10 carbons or an oxirane group, an alpha-N-[2-(3,4-dimethoxyphenyl)ethyl]aminomethyl)-beta-ethanol group or a 3-(2-methylpropoxy)-2-(1-pyrrolidinyl)propyl group; and $R^2$ is hydrogen, alkoxy of 1 to 6 carbons, alkyl of 1 to 6 carbons, trifluoromethyl, halo, nitro, hydroxy or dialkylamino of 2 to 10 carbons, and the pharmaceutically-acceptable acid-addition salts thereof.

2. The benzodiazepine of claim 1, wherein X is oxygen.

3. The benzodiazepine of claim 1, wherein X is two hydrogen atoms.

4. The benzodiazepine of claim 1, wherein $R^1$ is methyl, ethyl, n-propyl, iso-propyl, n-butyl, sec-butyl, iso-butyl, t-butyl, pentyl or hexyl.

5. The benzodiazepine of claim 1, wherein $R^2$ is methoxy, ethoxy, iso-propoxy, methyl, ethyl, tert-butyl, fluoro, chloro, bromo, iodo, dimethylamino or N-ethyl-N-methylamino.

6. The benzodiazepine of claim 1, wherein said salts are formed with an acid selected from the group consisting of hydrochloric, hydrobromic, hydroiodic, perchloric, sulfuric, nitric, phosphoric, acetic, propionic, glycolic, lactic, pyruvic, malonic, succinic, maleic, fumaric, malic, tartaric, citric, benzoic, cinnamic, madelic, methanesulfonic, ethanesulfonic, hydroxyethanesulfonic, benzenesulfonic, p-toluene sulfonic, cyclohexanesulfamic, salicylic, p-amino-salicylic, 2-phenoxybenzoic, 2-acetoxybenzoic or a salt made with saccharin.

7. The benzodiazepine of claim 1, wherein said benzodiazepine is selected from the group consisting of:

6H-indolo[2,1-c][1,4]benzodiazepin-12(11H)-one;
11-methyl-6H-indolo[2,1-c][1,4]benzodiazepin-12(11H)-one;
11,12-dihydro-6H-indolo[2,1-c][1,4]benzodiazepine;
11,12-dihydro-11-oxiranylmethyl-6H-indolo[2,1-c][1,4]benzodiazepine;
alpha-(N-[2,(3,4-dimethoxyphenyl)ethyl]aminomethyl)-11,12-dihydro-6H-indolo[2,1-c][1,4]benzodiazepine-11-ethanol;
11,12-dihydro-11-[3-(2-methylpropoxy)-2-(1-pyrrolidinyl)propyl]-6H-indolo[2,1-c][1,4]benzodiazepine;
11,12-dihydro-11-dimethylaminopropyl-6H-indolo[2,1c][1,4]benzodiazepine;
11-cyanomethyl-6H-indolo[2,1-c][1,4]benzodiazepine-12(11H)-one;
N,N-dimethyl-6H-indolo[2,1-c][1,4]benzodiazepin-12(11H)-one-11-propanamine;
3-methoxy-6H-indolo[2,1-c][1,4]benzodiazepin-12(11H)-one;
3-methoxy-N,N-dimethyl-6H-indolo[2,1-c][1,4]benzodiazepin-12(11H)-one-11-propanamine;
11-hexyl-6H-indolo[2,1-c][1,4]benzodiazepin-12(11H)-one; and
11-hexyl-11,12-dihydro-6H-indolo[2,1-c][1,4]benzodiazepine.

8. A pharmaceutical composition which comprises an amount of a benzodiazepine of claim 1 effective against hypertension in association with a pharmaceutically acceptable diluent or carrier.

9. A method of alleviating hypertension in a mammal which comprises administering to the mammal the pharmaceutical composition of claim 8.

10. The method of claim 9, wherein said mammal is a human.

* * * * *